United States Patent [19]
Dryden, Jr. et al.

[11] 4,155,906
[45] May 22, 1979

[54] PROCESS FOR PREPARING STEROIDAL 3-OXO-4,6-DIENES SUCH AS 17-HYDROXY-3-OXO-17α-PREGNA-4,6-DIENE-21-CARBOXYLIC ACID γ-LACTONE

[75] Inventors: Hugh L. Dryden, Jr., Deerfield; Gayle M. Webber, Wilmette, both of Ill.

[73] Assignee: G. D. Searle & Co., Skokie, Ill.

[21] Appl. No.: 856,886

[22] Filed: Dec. 2, 1977

[51] Int. Cl.$^2$ ............................................. C07J 19/00
[52] U.S. Cl. ................................................. 260/239.57
[58] Field of Search ..................................... 260/239.57

[56]  References Cited
U.S. PATENT DOCUMENTS
3,919,198  11/1975  Warnant et al. ................ 260/239.57

OTHER PUBLICATIONS
Syhora et al., "Collection Czechoslov. Chem. Commun.", 31, (1966), p. 2768.
"Organic Reactions in Steroid Chemistry", by Fried et al., pp. 285 and 293.

Primary Examiner—Elbert L. Roberts
Attorney, Agent, or Firm—John M. Brown

[57] ABSTRACT

A process for preparing 17-hydroxy-3-oxo-17α-pregna-4,6-diene-21-carboxylic acid γ-lactone by contacting 17-hydroxy-3-oxy-17α-pregna-3,5-diene-21-carboxylic acid γ-lactone with an appropriate halogenating agent in the presence of an amine base, the corresponding hydrohalide salt thereof, and approximately 1–2 molar equivalents (relative to the lactonic starting material) of water, using a cold solvent as the contact medium, and heating the resultant mixture with a dehydrohalogenating agent, is disclosed.

5 Claims, No Drawings

PROCESS FOR PREPARING STEROIDAL 3-OXO-4,6-DIENES SUCH AS 17-HYDROXY-3-OXO-17α-PREGNA-4,6-DIENE-21-CARBOXYLIC ACID γ-LACTONE

This invention relates to an improved process for preparing steroidal 3-oxo-4,6-dienes such as, and especially, 17-hydroxy-3-oxo-17α-pregna-4,6-diene-21-carboxylic acid γ-lactone, a compound valuable not only as an intermediate to the well-known antimineralocorticoid, spironolactone (U.S. Pat. No. 3,013,012), but similarly useful (U.S. Pat. No. 2,900,383).

The process to which this invention relates is distinguished from the prior art in one or more of the following particulars:

(1) It utilizes relatively inexpensive and readily available 3-oxy-3,5-dienes as the steroidal starting materials.

(2) It affords unpredictably high yields and good throughput.

(3) It is substantially free of undesirable side reactions and tarry by-products.

(4) It obviates the isolation and/or onerous manipulation of noxious intermediates.

Various procedures have been described in the literature for the preparation of steroidal 3-oxo-4,6-dienes from 3-oxy-5-enes. See, for example, U.S. Pat. Nos. 3,270,008, 3,413,289, and 3,682,894. Also, Langbein et al. in E. Germ. No. 34924 disclosed a multi-step preparation of 3-oxo-4,6-dienes from 3-oxo-6-oxy steroids. With the recent dramatically-improved accessibility of androst-4-ene-3,17-dione via degradative fermentation of steroids (U.S. Pat. No. 3,759,791), however, the utilization of such 3-oxo-4-enes and the 3,5-dienol ethers and esters easily obtainable therefrom as starting materials for the preparation of corresponding 3-oxo-4,6-dienes became a primary concern of those skilled in the involved art.

The use of manganese dioxide or 2,3,5,6-tetrachloro-2,5-cyclohexadiene-1,4-dione to convert a steroidal 3-oxo-4-ene or 3,5-dienol ether/ester thereof to the corresponding 3-oxo-4,6-diene is, of course, well-known in the art. See, for example, U.S. Pat. Nos. 2,900,383, 2,946,809, 3,137,690, 3,193,803, 3,257,390 and 3,968,132; Belg. No. 585,544; Can. No. 739,463; Germ. Offen. Nos. 2,404,946, 2,404,947, and 2,404,948; J. Org. Chem., 24, 1109 (1959); and Khim-Farm. Zh., 3, 10 (1969). Unfortunately, this procedure is commonly characterized by low yields and the formation of tarry by-products. Moreover, the uniquely-activated grade of manganese dioxide prescribed for this use is manifestly disadvantageous.

Another and perhaps heretofore preferred procedure for converting a steroidal 3-oxo-4-ene dienol ether/ester to the corresponding 3-oxo-4,6-diene comprises halogenating at carbon atom 6, isolating or otherwise laboriously manipulating the halo intermediate, which is thereupon dehydrohalogenated to afford the desired product. See, for example, Steroids, 1, 233 (1963); Collection Czechoslov. Chem. Commun., 31, 2768 (1966); J. Amer. Chem. Soc., 82, 1230 (1960); and J. Med. Chem., 6, 198 (1963). This prior art procedure calls for the presence of acetic acid and/or sodium acetate plus water, during halogenation, in amounts which dictate isolation or comparable manipulation of the resultant 6-halo intermediate prior to dehydrohalogenation in order to avoid undesirable side reactions. Since such 6-halo steroids are not only skin irritants, but typically difficult to filter out of the halogenation mixture, wash, and dry, their isolation is correspondingly burdensome. So too is the alternative offered, which involves separating the organic phase of the halogenation mixture and concentrating it as rapidly as possible by vacuum distillation at less than 20° C., extracting the aqueous phase with a limited quantity of 1,1'-oxybisethane; combining the extract with the concentrate; and washing, drying and filtering the resultant solution. Yields via this procedure appear generally to range from 64 to 77% of theory, based on product of unspecified purity.

The instant invention—illustratively applied to the preparation of 17-hydroxy-3-oxo-17α-pregna-4,6-diene-21-carboxylic acid γ-lactone from a 3,5-dienol ether or ester of 17-hyroxy-3-oxo-17α-pregn-4-ene-21-carboxylic acid γ-lactone—comprises contacting 3-ethoxy-17-hydroxy-17α-pregna-3,5-diene-21-carboxylic acid γ-lactone with a halogenating agent in the presence of an amine base, the corresponding hydrohalide salt thereof, and approximately 1–2 molar equivalents (relative to the lactonic starting material) of water, using a cold solvent as the contact medium, and heating the resultant mixture with a dehydrohalogenating agent. Separation, by whatever means, of the 6-halo intermediate formed in process, is obviated.

Appropriate halogenating agents include, but are not necessarily limited to, bromine, 1,3-dibromo-5,5-dimethyl-2,4-imidazolidinedione, 1-bromo-2,5-pyrrolidinedione, and N-bromoacetamide in an amount just sufficient to effect the indicated halogenation. Excess bromine can be removed via contact with a scavenger such as 2,4-pentanedione or, preferably, sulfur dioxide. Halogenation is ordinarily carried out at temperatures of the order of 5° C. or below to preclude the possibility of adversely affecting the quality of the final product.

Appropriate amine bases include, but are not necessarily limited to, pyridine and 2-methylpyridine in an amount slightly greater than that required to neutralize any acid formed in process. Among these bases, 2-methylpyridine is preferred.

The hydrohalide salt called for need not be added as such. It can be provided by interaction of the prescribed amine bases with hydrogen halide formed in situ or added in appropriately-concentrated aqueous solution. The function of the salt is to inhibit side reactions; and, accordingly, the amount incorporated need not be explicitly delimited.

Perhaps the most critical feature of the instant invention is the amount of water used. A minimum of 1 mole for each mole of steroid halogenated and a maximum of twice that amount appear to represent satisfactory operating limits, with 1.85 moles of water for each mole of steroid being preferable when the steroid is 3-ethoxy-17-hydroxy-17α-pregna-3,5-diene-21-carboxylic acid γ-lactone.

Appropriate solvents include, but are not necessarily limited to, N-substituted amides such as N,N-dimethylformamide, N,N-dimethylacetamide, N,N-diethylacetamide, N-methyl-2-pyrrolidone, and N-fromylpiperidine, among which N,N-dimethylformamide is preferred.

Among the various dehydrohalogenating agents known in the art, lithium bromide is preferred.

It is desirable to maintain an effectively inert atmosphere throughout the process, and especially during dehydrohalogenation.

Where an exceptionally pure product is required, and the product is a lactone, it is generally advantageous to heat the reaction mixture first with excess aqueous potassium hydroxide and then with sufficient hydrochloric acid to adjust the pH to approximately 1, prior to isolation.

The following examples describe in detail diverse embodiments of the process of this invention in illustrative situations. However, it will be apparent to those skilled in the art that many modifications, both of materials and of methods, may be practiced without departing from the purpose and intent of this disclosure. Throughout the examples hereinafter set forth, temperatures are given in degrees centigrade and relative amounts of materials in parts by weight, except as otherwise noted. Yields are expressed as percent of theory, based on the amount of 3-oxo-4,6-diene obtained, as determined by its ultraviolet spectrum.

EXAMPLE 1

To a mixture of 257 parts of 3-ethoxy-17-hydroxy-17α-pregna-3,5-diene-21-carboxylic acid γ-lactone, 147 parts of 2-methylpyridine, 23 parts of water, and 512 parts of N,N-dimethylformamide at 0°–5° in a nitrogen atmosphere is added, with stirring during approximately 10 min., a solution of 113 parts of bromine in 244 parts of N,N-dimethylformamide. The resultant solution is stirred for approximately 5 min., whereupon 5 parts of 2,4-pentanedione is added. Stirring under nitrogen is continued for a further 3 min., at which point 59 parts of lithium bromide is added. The resultant solution is heated at 95°–100° under nitrogen for 2 hr. with continued stirring, then cooled to, and maintained at, 90°–100° with continued stirring while a solution of 101 parts of potassium hydroxide in 100 parts of water is added during approximately 5 min. Volatile liquids are stripped from the resultant mixture by vacuum distillation at ≦ 100°. The pasty distilland is cooled to around 60°, whereupon 304 parts of methanol is added. The resultant mixture is heated at the boiling point under reflux until a thin slurry eventuates, at which point a solution of 67 parts of 85% potassium hydroxide in 500 parts of water is added. Heating at the boiling point under reflux with stirring is continued for a further 20 min., whereupon 167 parts of concentrated hydrochloric acid is added. Stirring at the boiling point under reflux is continued for still a further 30 min., whereupon the methanol is stripped by vacuum distillation while 892 parts of water is concurrently added. The distilland is then cooled to room temperature, at which point insoluble solids are filtered out, washed with water until the pH of the washings approximates 5–6, and finally dried at 70° overnight. The product thus isolated is 17-hydroxy-3-oxo-17α-pregna-4,6-diene-21-carboxylic acid γ-lactone. A representative yield via this procedure is 93.6% of theory.

EXAMPLE 2

To a solution of 64 parts of 2-methylpyridine in 384 parts of N,N-dimethylformamide at 0° is added, with stirring, 23 parts of 48% hydrobromic acid. To the resultant solution, cooled to and maintained at −15°, is added, with stirring, 135 parts of 3-ethoxy-17-hydroxy-17αprena-3,5-diene-21-carboxylic acid γ-lactone. To the resultant slurry is added, portionwise with continued stirring, approximately 55 parts of 1,3-dibromo-5,5-dimethyl-2,4-imidazolidinedione, temperature being permitted to rise to 0° during the course of the addition. The resultant orange solution is stirred at 0° for approximately 10 min., whereupon the following additions thereto are consecutively effected, stirring being continuous throughout: (1) that quantity of a solution of 10 parts of sulfur dioxide in 19 parts of N,N-dimethylformamide just sufficient to induce a negative starch-iodide test; (2) an additional 1.2 parts of the sulfur dioxide solution; (3) 31 parts of lithium bromide. The resultant mixture is stirred at 95°–100° in a nitrogen atmosphere for 2 hr., then cooled to 80° and thereupon consecutively diluted with: (1) a solution of 35 parts of 85% potassium hydroxide in 35 parts of water; (2) 17 parts of water. The resultant mixture is stripped of the bulk of the solvent by vacuum distillation, and the pasty distilland is thereupon mixed with 162 parts of methanol. This mixture is warmed and stirred for about 10 min., at which point a solution of 38 parts of 85% potassium hydroxide in 157 parts of water is added. The resultant mixture is heated at the boiling point under reflux with stirring for 20 min., whereupon 27 parts of water and 22 parts of methanol are consecutively added. To the mixture thus obtained, preliminarily cooled to 35°, is added sufficient concentrated hydrochloric acid to lower the pH to 1. The resultant mixture is heated to the boiling point and then stripped of methanol by vacuum distillation while 173 parts of water is concurrently added. The distilland is thereupon cooled to 25° and then mixed with 338 parts of water. Insoluble solids are separated by filtration, washed with water, and dried at 60°. The product thus isolated is 17-hydroxy-3-oxo-17α-pregna-4,6-diene-21-carboxylic acid γ-lactone. A representative yield via this procedure is 90.9% of theory.

EXAMPLE 3

To a solution of 172 parts of 2-methylpyridine in 855 parts of N,N-dimethylformamide at 0° is added, with stirring, 52 parts of 48% hydrobromic acid. To the resultant solution, cooled to and maintained at −25°, is added, with stirring, 300 parts of 3-ethoxy-17-hydroxy-17α-pregna-3,5-diene-21-carboxylic acid γ-lactone. To the resultant slurry is added, portionwise with continued stirring, approximately 118 parts of N-bromoacetamide, temperature being permitted to rise to 0° during the course of the addtion. The resultant solution is stirred at 0° for approximately 10 min., whereupon the following additions thereto are consecutively effected, stirring being continuous throughout: (1) that quantity of a solution of 10 parts of sulfur dioxide in 19 parts of N,N-dimethylformamide just sufficient to induce a negative starch-iodide test; (2) an additional 3 parts of the sulfur dioxide solution; (3) 69 parts of lithium bromide. The resultant mixture is stirred at 98° in a nitrogen atmosphere for 2 hr., then cooled to 30° and mixed with a solution of approximately 16 parts of 85% potassium hydroxide in 30 parts of water. The resultant mixture is stripped of solvent by vacuum distillation, and the distilland is thereupon mixed with 360 parts of methanol. This mixture is warmed and stirred for about 10 min., at which point a solution of approximately 71 parts of 85% potassium hydroxide in 350 parts of water is added. The resultant mixture is heated at the boiling point under reflux with stirring for 20 min., whereupon 60 parts of water and 48 parts of methanol are consecutively added. To the mixture thus obtained, at temperatures between 32° and 45°, is added sufficient concentrated hydrochloric acid to lower the pH to 1. The resultant mixture is heated to the boiling point and then stripped of methanol by vacuum distillation while 384 parts of water is concurrently added. The distilland is thereupon cooled to 30°, whereupon insoluble solids are filtered out, washed with water, and dried. The product thus isolated is 17-hydroxy-3-oxo-17α-pregna-4,6-diene-21-carboxylic acid γ-lactone. A representative yield via this procedure is 94.8% of theory.

EXAMPLE 4

To a solution of 95 parts of 2-methylpyridine in 570 parts of N,N-dimethylformamide at 0° is added, with stirring, 35 parts of 48% hydrobromic acid. To the resultant solution, cooled to and maintained at −25°, is added, with stirring, 200 parts of 3-ethoxy-17-hydroxy-17α-pregna-3,5-diene-21-carboxylic acid γ-lactone. To the resultant solution is added, portionwise with continued stirring, 101 parts of 1-bromo-2,5-pyrrolidinedione, temperature being permitted to rise to 0° during the course of the addition. The resultant orange solution is stirred at 0° for 12 min., whereupon the following additions thereto are consecutively effected, stirring being continuous throughout: (1) that quantity of a solution of 10 parts of sulfur dioxide in 19 parts of N,N-dimethylformamide just sufficient to induce a negative starch-iodide test; (2) an additional 1.8 parts of the sulfur dioxide solution; (3) 46 parts of lithium bromide. The resultant mixture is stirred at 97° in a nitrogen atmosphere for 2 hr., then cooled to 15° and mixed with a solution of approximately 52 parts of 85% potassium hydroxide in 100 parts of water. The resultant mixture is stripped of solvent by vacuum distillation, and the distilland is thereupon mixed with 240 parts of methanol. This mixture is warmed and stirred for about 10 min., at which point a solution of approximately 41 parts of 85% potassium hydroxide in 200 parts of water is added. The resultant mixture is heated at the boiling point under reflux with stirring for 20 min., then cooled to approximately 40°. Sufficient concentrated hydrochloric acid to lower the pH to 1 is added, whereupon methanol is stripped by vacuum distillation while 300 parts of water is concomitantly introduced. The distilland is then diluted with a further 200 parts of water and cooled to 25°, at which point insoluble solids are filtered out, washed with water, and dried in warm air. The product thus isolated is 17-hydroxy-3-oxo-17α-pregna-4,6-diene-21-carboxylic acid γ-lactone. A representative yield via this procedure is 92.1% of theory.

What is claimed is:

1. A process for preparing 17-hydroxy-3-oxo-17α-pregna-4,6-diene-21-carboxylic acid γ-lactone which comprises contacting 3-ethoxy-17-hydroxy-17α-pregna-3,5-diene-21-carboxylic acid γ-lactone with a brominating agent selected from among bromine, 1,3-dibromo-5,5-dimethyl-2,4-imidazolidinedione, 1-bromo-2,5-pyrrolidinedione, and N-bromacetamide in the presence of 2-methylpyridine, 2-methylpyridine hydrobromide, and approximately 1–2 molar equivalents (relative to the lactonic starting material) of water, using cold N,N-dimethylformamide as the contact medium, and heating the resultant mixture with lithium bromide, said process being carried out in an effectively inert atmosphere.

2. A process according to claim 1 wherein the 17-hydroxy-3-oxo-17α-pregna-4,6-diene-21-carboxylic acid γ-lactone prepared thereby is further purified by consecutively heating it in situ with excess aqueous potassium hydroxide and sufficient hydrochloric acid to adjust the pH to approximately 1.

3. A process according to claim 2 wherein the brominating agent is bromine.

4. A process according to claim 2 wherein the brominating agent is 1,3-dibromo-5,5-dimethyl-2,4-imidazolidinedione.

5. A process according to claim 4 wherein the 2-methylpyridine, 2-methylpyridine hydrobromide, and water called for is provided by contacting 2-methylpyridine with hydrobromic acid.

* * * * *